United States Patent
Tulchinsky et al.

(10) Patent No.: US 9,650,321 B2
(45) Date of Patent: May 16, 2017

(54) RENEWABLE SURFACTANTS DERIVED FROM SUGAR ALCOHOLS

(75) Inventors: Michael L. Tulchinsky, Midland, MI (US); Sze-Sze Ng, Midland, MI (US); Cynthia L. Rand, Sanford, MI (US)

(73) Assignee: Dow Global Technologies LLC, Midland, MI (US)

( * ) Notice: Subject to any disclaimer, the term of this patent is extended or adjusted under 35 U.S.C. 154(b) by 270 days.

(21) Appl. No.: 14/007,534

(22) PCT Filed: Feb. 22, 2012

(86) PCT No.: PCT/US2012/026013
§ 371 (c)(1),
(2), (4) Date: Sep. 25, 2013

(87) PCT Pub. No.: WO2012/148530
PCT Pub. Date: Nov. 1, 2012

(65) Prior Publication Data
US 2014/0316148 A1    Oct. 23, 2014

Related U.S. Application Data

(60) Provisional application No. 61/479,275, filed on Apr. 26, 2011.

(51) Int. Cl.
| | | |
|---|---|---|
| *C07D 307/12* | (2006.01) | |
| *C07D 307/20* | (2006.01) | |
| *C07C 41/01* | (2006.01) | |
| *C07C 43/13* | (2006.01) | |

(52) U.S. Cl.
CPC .............. *C07C 41/01* (2013.01); *C07C 43/13* (2013.01); *C07D 307/12* (2013.01); *C07D 307/20* (2013.01)

(58) Field of Classification Search
CPC .... C07D 307/12; C07D 307/20; C07C 41/61; C07C 43/13; C07C 41/01
See application file for complete search history.

(56) References Cited

U.S. PATENT DOCUMENTS

| | | |
|---|---|---|
| 3,839,318 A | 10/1974 | Mansfield |
| 4,929,374 A | 5/1990 | De Jong et al. |
| 5,644,041 A | 7/1997 | Johansson |
| 5,744,053 A | 4/1998 | Kaimai |
| 5,922,239 A | 7/1999 | Nakagawa et al. |
| 6,441,196 B2 | 8/2002 | Delgado et al. |
| 9,067,863 B2 | 6/2015 | Ernst et al. |
| 2014/0316148 A1 | 10/2014 | Tulchinsky et al. |

FOREIGN PATENT DOCUMENTS

| | | |
|---|---|---|
| EP | 0601836 A2 | 6/1994 |
| EP | 1619237 A1 | 1/2006 |
| JP | S59-083173 | 5/1984 |
| JP | S61-285232 A | 12/1986 |
| JP | S63-035525 A | 2/1988 |
| JP | S64-069391 A | 3/1989 |
| JP | H06-266076 A | 9/1994 |
| JP | 07239542 A | 9/1995 |
| JP | 07239542 | 12/1995 |
| JP | 09-095478 | 4/1997 |
| JP | 2001031611 | 2/2001 |
| JP | 2001-172476 | 6/2001 |
| JP | 2003-213088 | 7/2003 |
| JP | 2004-175710 A | 6/2004 |
| JP | 2004-175711 A | 6/2004 |
| JP | 2004175710 | 6/2004 |
| JP | 2004175711 | 6/2004 |
| JP | 2008-516940 A | 5/2006 |
| JP | 2010-536914 A | 12/2010 |
| WO | 2009126852 | 10/2009 |
| WO | 2010027663 | 3/2010 |
| WO | 2010027663 A1 | 3/2010 |
| WO | 2011106194 | 9/2011 |

OTHER PUBLICATIONS

Velimirovic et al., caplus an 1997:27245, 1997.*
Nicotra et al., 1989, caplus an 1989:453657.*
Hana Jirglova et al, "Chemical 1-12 Interactions of Surface-Active Agents with Growing Resorcinol-Formaldehyde Gels," 2010, LANGMUIR, 26:16103-16109.
Francesco Nicotra at al, "An interesting example of complementary regioselective acylation of secondary hydroxyl groups by different lipases," Tetrahedron Letters 1989, 30:1703-1704.
Giacometti, "Process for Preparing Nonionic Surfactant Sorbitan Fatty Acid Esters with and without Food Chemistry," (1996) 44(12), 3950-3954.
Duclos, "A Simple Conversion of Polyols into Anhydroalditols" Synthesis (1994) (10):1087-1090.
Soltzberg, Hexitol Anhydrides; Synthesis and Structure of Arlitan, the 1,4-Monoanhydride of Sorbitol, Journal of Am. Chemistry Society (1946) 919-21.
International Search Report for PCT/US2012/026013, dated Aug. 20, 2012.
IUPAC Compendium of Chemical Terminology Gold Book; Version 2.3.3; Feb. 24, 2014, p. 60 of 1622.

* cited by examiner

*Primary Examiner* — Sun Jae Yoo
(74) *Attorney, Agent, or Firm* — Brooks, Cameron & Huebsch, PLLC

(57) ABSTRACT

Polyol ether compounds and processes for their preparation. A representative process comprises melting a polyol, and reacting the molten polyol, a carbonyl compound, and hydrogen in the presence of a hydrogenation catalyst to provide the polyol ether. The polyol ether has surfactant properties.

5 Claims, 3 Drawing Sheets

RENEWABLE SURFACTANTS DERIVED FROM SUGAR ALCOHOLS

CROSS REFERENCE TO RELATED APPLICATION

This application claims priority to International Patent Application No. PCT/US2012/026013, filed Feb. 22, 2012, which claims priority to U.S. Provisional Patent Application No. 61/479,275 filed on Apr. 26, 2011, all of which are hereby incorporated herein by reference in their entireties.

FIELD

This invention relates to surfactant compounds. This invention also relates to processes for making surfactant compounds by reacting a polyol with a carbonyl compound and hydrogen.

BACKGROUND

Many detergent compositions require 100% renewable surfactants with renewable carbon indexes equal to one. The renewable carbon index of a molecule is obtained by dividing the number of the molecule's carbons derived from renewable sources by the total number of carbons. Examples of such surfactants include certain classes of compounds, such as alkyl polyglucosides (APG). APG surfactants are often used commercially; however, their cleaning performance generally does not match that of non-renewable anionic surfactants. Additionally, APG surfactants are susceptible to hydrolysis in acidic media.

A need exists, therefore, for renewable surfactants that are resistant to hydrolysis in a broad range of pH and with improved cleaning performances and for processes for making such renewable surfactants.

BRIEF SUMMARY

In one aspect, an illustrative embodiment provides a process for making polyol ethers. This process comprises melting a polyol and reacting the molten polyol, a carbonyl compound, and hydrogen in the presence of a hydrogenation catalyst to provide the polyol ether. The resulting polyol ether can be represented by the formula I:

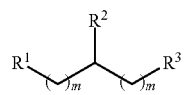

in which $R^1$ is $(C_1-C_{15})$ alkyl, $(C_2-C_{15})$ alkenyl, aryl-$(C_1-C_{15})$ alkyl, aryl-$(C_2-C_{15})$ alkenyl, $(C_3-C_{15})$ cycloalkyl, $(C_3-C_{12})$ cycloalkyl-$(C_1-C_6)$ alkyl, $(C_3-C_{12})$ cycloalkyl-$(C_3-C_{12})$ cycloalkyl, or

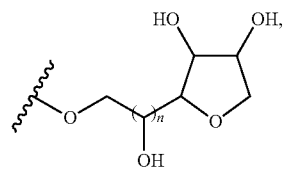

or $R^1$ and $R^2$ together with the carbon to which they are attached form a $(C_3-C_{15})$ cycloalkyl ring, and wherein the alkyl, alkenyl, aryl, and cycloalkyl groups of $R^1$ and $R^2$ are optionally substituted with 1, 2, or 3 groups independently selected from —OH, halogen, dialkylamino, carbon-carbon double bond, $(C_1-C_6)$ alkyl, aldehyde, ketone, carboxylic acid, ester, ether, alkynyl, dialkylamide, anhydride, carbonate, epoxide, lactone, lactam, thioether, thiol, and phenol, $R^2$ is hydrogen, $(C_1-C_{15})$ alkyl, $(C_2-C_{15})$ alkenyl, aryl-$(C_1-C_{15})$ alkyl, aryl-$(C_2-C_{15})$ alkenyl, $(C_3-C_{15})$ cycloalkyl, $(C_3-C_{12})$ cycloalkyl-$(C_1-C_6)$ alkyl, or cycloalkyl-$(C_3-C_{12})$ cycloalkyl, or $R^1$ and $R^2$ together with the carbon to which they are attached form a $(C_3-C_{15})$ cycloalkyl ring, and wherein the alkyl, alkenyl, aryl, and cycloalkyl groups of $R^1$ and $R^2$ are optionally substituted with 1, 2, or 3 groups independently selected from —OH, halogen, dialkylamino, carbon-carbon double bond, $(C_1-C_6)$ alkyl, aldehyde, ketone, carboxylic acid, ester, ether, alkynyl, dialkylamide, anhydride, carbonate, epoxide, lactone, lactam, thioether, thiol, and phenol, and $R^3$ is

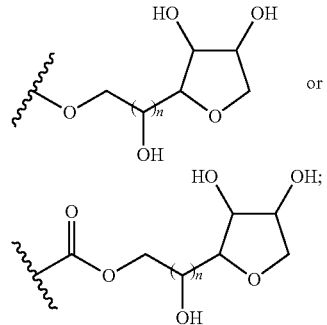

and wherein m is independently 0-8 and wherein n is independently 0 or 1. The $(C_1-C_{15})$ alkyl can be mono-cyclic, bi-cyclic, or tri-cyclic.

In other aspects, the resulting polyol ether can be represented by the formula I:

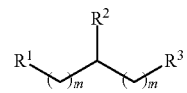

in which $R^1$ is $(C_1-C_{15})$ alkyl, $R^2$ is hydrogen, $R^3$ is

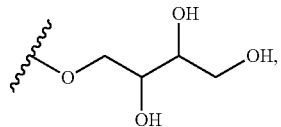 [SMILES: *OCC(O)C(O)CO]

and m is 0.

In another aspect, compounds of formula I are provided.

DETAILED DESCRIPTION

Figure 1:
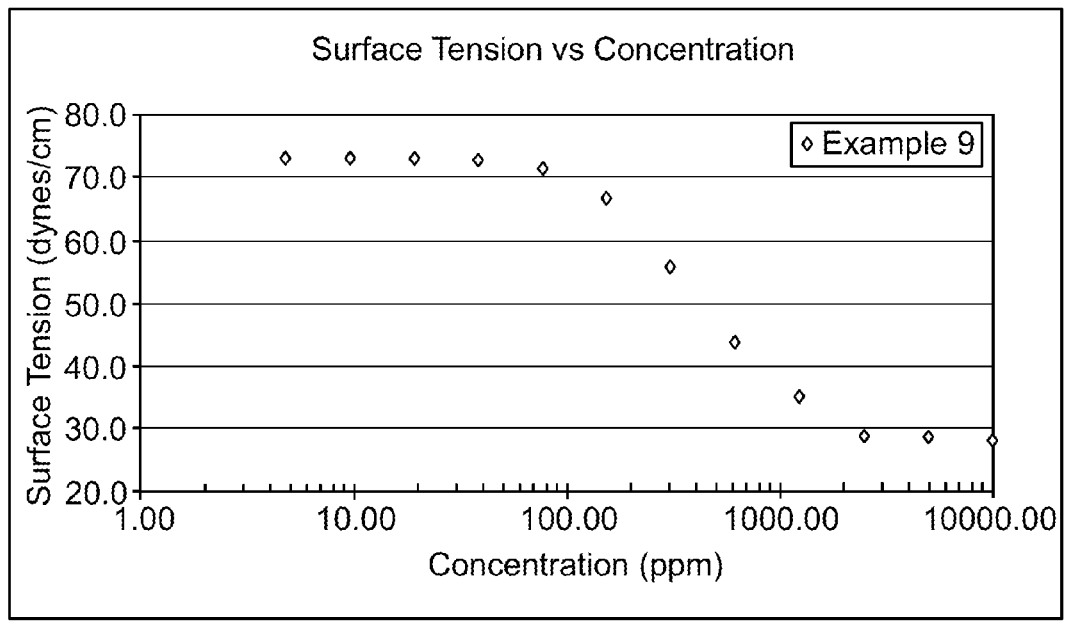
FIG. 1 is a graph of surface tension versus concentration for Example 9.

In one aspect, this invention provides a process for making polyol ethers. The resulting polyol ethers may be sugar alcohol ethers, preferably with surfactant properties. The process comprises: melting a polyol and reacting the molten polyol and a carbonyl compound with hydrogen in the presence of a hydrogenation catalyst to provide the polyol ether, as shown in the scheme below.

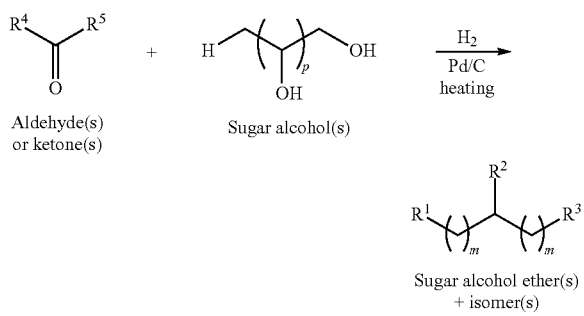

Aldehyde(s) or ketone(s)    Sugar alcohol(s)

Sugar alcohol ether(s) + isomer(s)

In the scheme above, $R^3$ is derived from the sugar alcohol. Melting the polyol prior to the reaction provides advantages over the prior art, including improved yields and improved selectivity. For example, melting the polyol prior to the reaction accelerates the initial carbonyl compound transformation to cyclic acetals in the presence of sugar alcohols, which minimizes the reduction of the carbonyl compounds to the corresponding alcohols.

The carbonyl compound for use in the process can be represented by formula II:

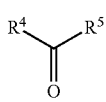

II wherein $R^4$ and $R^5$ are independently hydrogen, ($C_1$-$C_{15}$) alkyl, ($C_2$-$C_{15}$) alkenyl, aryl-($C_1$-$C_{15}$) alkyl, aryl-($C_2$-$C_{15}$) alkenyl, ($C_3$-$C_{15}$) cycloalkyl, ($C_3$-$C_{12}$) cycloalkyl-($C_1$-$C_6$) alkyl, ($C_3$-$C_{12}$) cycloalkyl-($C_3$-$C_{12}$) cycloalkyl, or $R^4$ and $R^5$ together with the carbon to which they are attached form a ($C_3$-$C_{15}$) cycloalkyl ring, and wherein the alkyl, alkenyl, aryl, and cycloalkyl groups of $R^4$ and $R^5$ are optionally substituted with 1, 2, or 3 groups independently selected from —OH, halogen, dialkylamino, carbon-carbon double bond, an aromatic moiety, ($C_1$-$C_6$) alkyl, aldehyde, ketone, carboxylic acid, ester, ether, alkynyl, dialkylamide, anhydride, carbonate, epoxide, lactone, lactam, thioether, thiol, and phenol, provided that both $R^4$ and $R^5$ are not hydrogen.

In the alternative, the carbonyl compound may be:

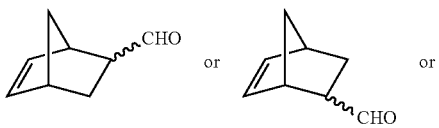

-continued

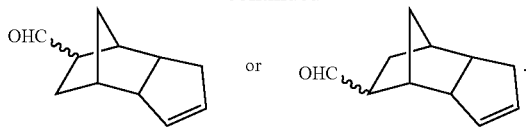

Preferred substituents on $R^4$ and $R^5$ are carbon-carbon double bond, an aromatic moiety, aldehyde, and ketone. More preferred substituents on $R^4$ and $R^5$ are carbon-carbon double bond, an aldehyde, and ketone.

Preferred compounds include those wherein $R^4$ is ($C_1$-$C_{10}$) alkyl and $R^5$ is hydrogen and even more preferably, wherein $R^4$ is ($C_5$-$C_7$) alkyl and $R^5$ is hydrogen. In an illustrative embodiment, the carbonyl compound may be a linear, branched, or cyclic ($C_6$-$C_{12}$) aldehyde, for example, hexanal, heptanal, cyclohexanecarbaldehyde, octanal, 2-ethylhexanal, 2-propylheptanal, nonanal, decanal, undecanal, dodecanal, and corresponding $C_6$-$C_{12}$ ketones along with their isomers and derivatives used as pure compounds or as mixtures. Examples of corresponding ($C_6$-$C_{12}$) ketones include 2-hexanone, 2-heptanone, cyclohexanone, 2-octanone, 3-methylheptan-4-one, 3-methylheptan-2-one, 5-methylheptan-3-one, 5-methylheptan-2-one, 2-nonanone, 2-decanone, 2-undecanone, and 2-dodecanone. These carbonyl compounds may be substituted or unsubstituted, provided that any substituents do not interfere with the reductive etherification process. In some embodiments, the carbonyl compounds may contain a remote aromatic moiety or more than one carbonyl group. The aromatic moiety should be located away from the reaction center in order to not interfere with the reaction. An example of a carbonyl compound with a remote aromatic moiety includes cinnamaldehyde. In further embodiments, the aldehydes and ketones may also contain a function that will be reduced under the reaction conditions, for example, a double bond. The carbonyl compound may be derived from nature, such as, for example, heptanal obtained from castor oil, making the whole molecule entirely renewable. Other examples of carbonyl compounds derived from nature include terpenes, such as geranial and citral.

The polyol for uses in the process can be represented by formula III:

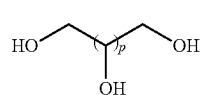

III wherein p is 2, 3 or 4.

In an illustrative embodiment, the polyol may be a sugar alcohol such as sorbitol, iditol, dulcitol, mannitol, xylitol, ribitol, or arabitol and their isomers used as pure compounds or mixtures. For example, mixtures of polyols with different numbers of carbons (e.g., $C_5$ and $C_6$) may be used, such as a mixture of sorbitol and xylitol. In another illustrative embodiment, the polyol may be a shorter chain sugar alcohol such as erythritol, threitol, or 1,2,3,4-butanetetrol, used as pure compounds or mixtures. When shorter chain sugar alcohols are used, the resulting compound is typically an open-chain polyol ether.

Representative carbonyl compounds and polyols for use in the process are shown in columns A and B of Table 1 below. Simple variations in carbon number or in the presence of double bonds that can undergo reduction are also generally incorporated into these teachings.

TABLE 1

Carbonyl compounds and polyols for use in the reductive etherification process

| | A (Carbonyl Compound) | B (Polyol) |
|---|---|---|
| 1 | Hexanal | Sorbitol |
| 2 | Heptanal | Xylitol |
| 3 | Octanal | Meso-erythritol |
| 4 | 2-ethylhexanal | Iditol |
| 5 | Cyclohexanecarbaldehyde | Dulcitol |
| 6 | Nonanal | Mannitol |
| 7 | Decanal | Ribitol |

TABLE 1-continued

Carbonyl compounds and polyols for use in the reductive etherification process

| | A (Carbonyl Compound) | B (Polyol) |
|---|---|---|
| 8 | Undecanal | Arabitol |
| 9 | Dodecanal | Threitol |
| 10 | (Z)-2-(Tetradeca-5,13-dien-1-yl)malonaldehyde | 1,2,3,4-butanetetrol |
| 11 | 9-formyloctadecanoic acid | |

Representative polyol ethers include the products produced by the following combinations of carbonyl compound (A) and polyol (B):

A1+B1
A2+B1
A3+B1
A1+B2
A2+B2
A3+B2
A1+B3
A2+B3
A3+B3
A4+B1
A1+(mixture of B1 and B2)
A2+(mixture of B1 and B2)
A3+(mixture of B1 and B2)
A4+(mixture of B1 and B2)
A10+B1
A11+B1

In certain aspects, the polyol ethers display surfactant properties. To provide good surfactant properties, the appropriate carbonyl compound and polyol will be selected to provide sufficient water solubility. For example, polyol ethers with large alkyl groups, such as $C_{16}$-$C_{18}$, are practically insoluble in water and not suitable as oil-in-water surfactants.

The molar ratio of polyol to carbonyl compound in the process is typically greater than 5:1, thus providing a large excess of the polyol. Using a large molar excess of polyol provides advantages such as improved yields and product selectivity. In a preferred embodiment, the molar ratio of polyol to carbonyl compound is at least 6:1, or at least 7:1. Even more preferably it is at least 8:1 or at least 9:1. There is no particular upper limit on the amount of excess polyol that is used, especially since the polyol can be recycled and reused. In some embodiments, it is preferred that the polyol to carbonyl compound molar ratio not exceed 100:1, more preferably not exceed 50:1.

In typical embodiments, the molten polyol and carbonyl compound are reacted with hydrogen in the presence of a hydrogenation catalyst. A non-reactive solvent may be used. However, since the excess molten sugar alcohol itself functions as a solvent, additional solvent is not needed and generally is not preferred.

Suitable hydrogenation catalysts may be Pd/C, with or without an additional metal as a second component. If an additional metal is used, it may be La or other lanthanides, Pd, Pt, Rh, or Ru. The catalyst pH as a five weight percent slurry with water may be acidic. The catalyst supports may be acidic and may comprise mesoporous carbon. A fixed bed or pellet catalyst may be used when the process is continuous. The catalyst loading for five weight percent Pd/C may be between about 0.01 and 30 weight percent, more preferably between about 0.1 and 20 weight percent, and even more preferably between about 5 and 10 weight percent relative to the carbonyl compound, depending on the structure of the components.

The reaction may be carried out at temperature of between about 30 and 300 degrees Celsius, more preferably between about 100 and 250 degrees Celsius, and even more preferably between about 150 and 220 degrees Celsius. The reaction pressure may be between about 0 and $2.07 \times 10^7$ Pa (0 and 3000 psi), more preferably between about $6.89 \times 10^5$ and $1.38 \times 10^7$ Pa (100 and 2000 psi), and even more preferably between about $1.38 \times 10^6$ and $8.27 \times 10^6$ Pa (200 and 1200 psi).

The reaction may be run from between a few minutes to about 24 hours, with 10 to 24 hours being preferred. The product(s) may be isolated from the reaction mixture by techniques well known to those skilled in the art, such as solvent extraction, distillation, and/or chromatography. For products that phase separate, decantation may be used.

Preferred polyol ethers prepared according to the process of the invention are of formula I:

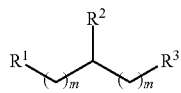

I in which $R^1$ is $(C_1$-$C_{15})$ alkyl, $(C_2$-$C_{15})$ alkenyl, aryl-$(C_1$-$C_{15})$ alkyl, aryl-$(C_2$-$C_{15})$ alkenyl, $(C_3$-$C_{15})$ cycloalkyl, $(C_3$-$C_{12})$ cycloalkyl-$(C_1$-$C_6)$ alkyl, $(C_3$-$C_{12})$ cycloalkyl-$(C_3$-$C_{12})$ cycloalkyl, or

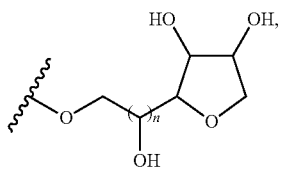

or $R^1$ and $R^2$ together with the carbon to which they are attached form a $(C_3$-$C_{15})$ cycloalkyl ring, and wherein the alkyl, alkenyl, aryl, and cycloalkyl groups of $R^1$ and $R^2$ are optionally substituted with 1, 2, or 3 groups independently selected from —OH, halogen, dialkylamino, carbon-carbon double bond, $(C_1$-$C_6)$ alkyl, aldehyde, ketone, carboxylic acid, ester, ether, alkynyl, dialkylamide, anhydride, carbonate, epoxide, lactone, lactam, thioether, thiol, and phenol, $R^2$ is hydrogen, $(C_1$-$C_{15})$ alkyl, $(C_2$-$C_{15})$ alkenyl, aryl-$(C_1$-$C_{15})$ alkyl, aryl-$(C_2$-$C_{15})$ alkenyl, $(C_3$-$C_{15})$ cycloalkyl, $(C_3$-$C_{12})$ cycloalkyl-$(C_1$-$C_6)$ alkyl, or cycloalkyl-$(C_3$-$C_{12})$ cycloalkyl, or $R^1$ and $R^2$ together with the carbon to which they are attached form a $(C_3$-$C_{15})$ cycloalkyl ring, and wherein the alkyl, alkenyl, aryl, and cycloalkyl groups of $R^1$ and $R^2$ are optionally substituted with 1, 2, or 3 groups independently selected from —OH, halogen, dialkylamino, carbon-carbon double bond, $(C_1$-$C_6)$ alkyl, aldehyde, ketone, carboxylic acid, ester, ether, alkynyl, dialkylamide, anhydride, carbonate, epoxide, lactone, lactam, thioether, thiol, and phenol, and $R^3$ is

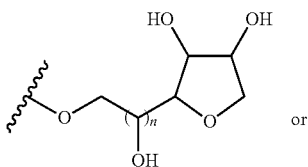

or

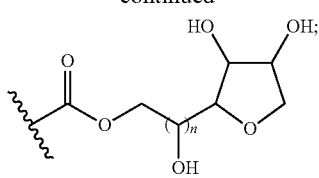

and wherein m is independently 0-8 and wherein n is independently 0 or 1. The $(C_1$-$C_{15})$ alkyl can be monocyclic, bi-cyclic, or tri-cyclic. Preferably, the cycloalkyl is cyclopropyl, cyclobutyl, cyclopentyl, cyclopentenyl, cyclohexyl, cyclohexenyl, cycloheptyl, and cyclooctyl.

In illustrative embodiments, $R^1$ is $(C_1$-$C_{15})$ alkyl, $(C_3$-$C_{15})$ cycloalkyl, $(C_3$-$C_{12})$ cycloalkyl-$(C_1$-$C_6)$ alkyl, $R^2$ is hydrogen, and $R^3$ is

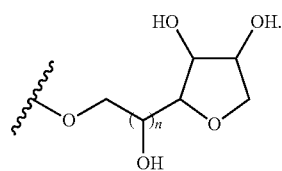

In other illustrative embodiments, $R^1$ is $(C_1$-$C_{15})$ alkyl, $R^2$ is hydrogen, $R^3$ is

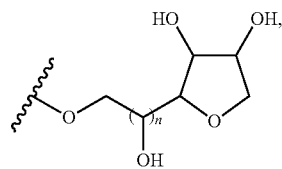

and m is 0.

Preferably, $R^1$ is $(C_1$-$C_{10})$ alkyl, and more preferably, $R^1$ is $(C_5$-$C_7)$ alkyl.

In yet other illustrative embodiments, the polyol ether is of formula I:

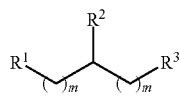

I in which $R^1$ is $(C_1$-$C_{15})$ alkyl, $R^2$ is hydrogen, $R^3$ is

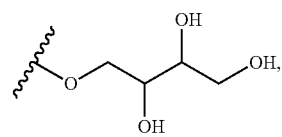 [SMILES: *OCC(O)C(O)CO]

and m is 0.

Preferred polyol ethers prepared by the process of the invention are as follows:

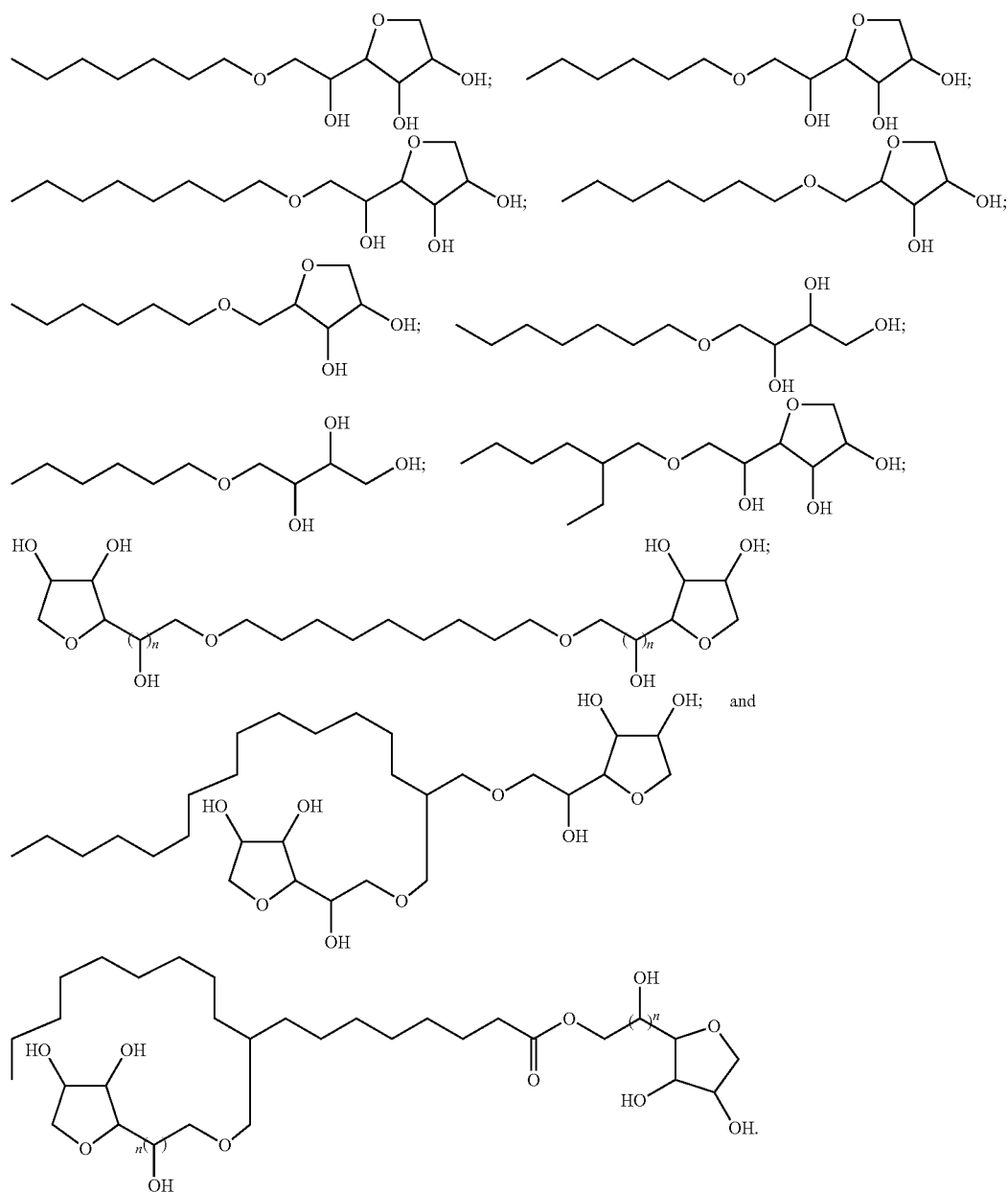
In a further aspect, the invention provides compounds selected from:
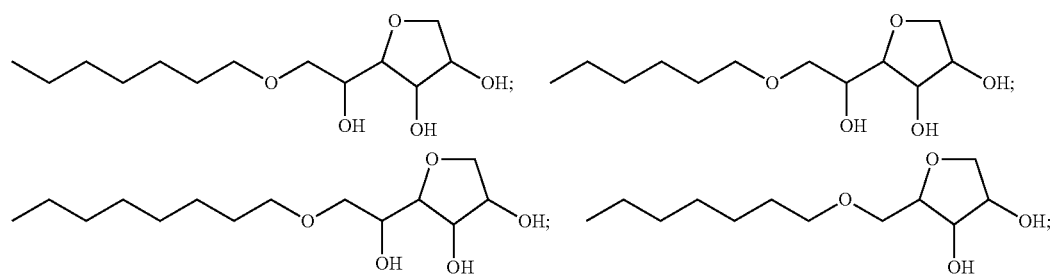

-continued

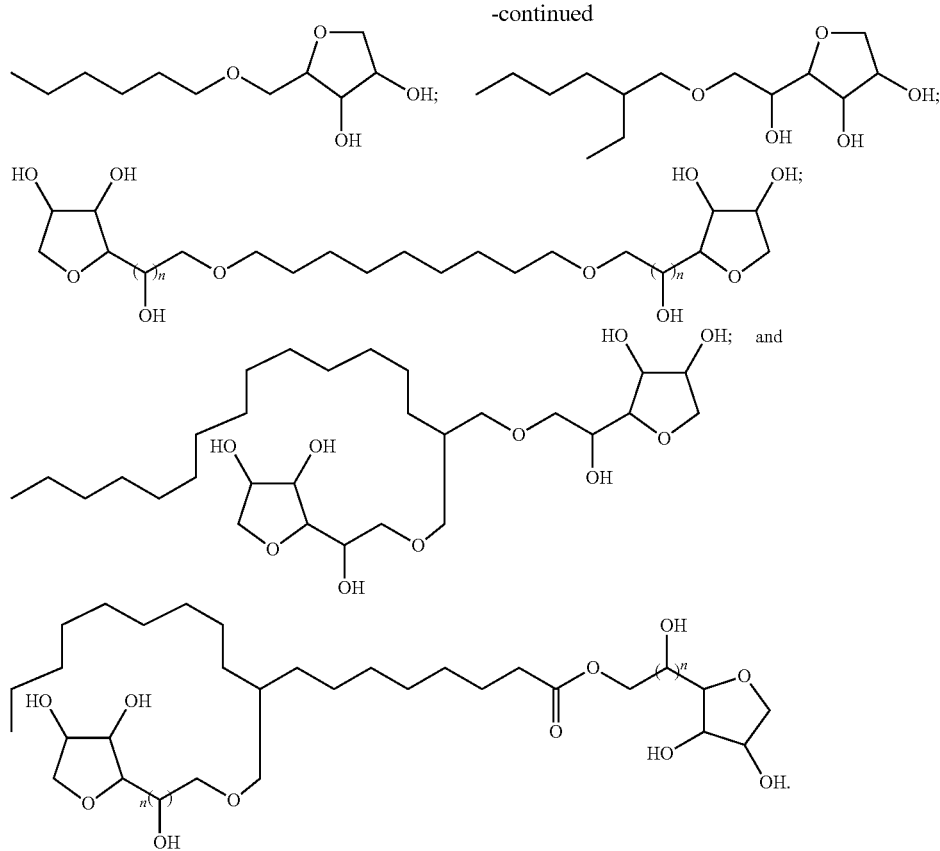

Preferred polyol ethers provide efficient hard surface cleaning comparable to that of known surfactants, such as TERGITOL™ 15-S-7 surfactant, a secondary alcohol ethoxylate. For example, surface tension in water of the compound may be less than about 0.03 N/m (30 dynes/cm) and the critical micelle concentration in water may be about 2500 parts per million. Furthermore, the grey scale value in a scrub test may be greater than 60.

"Alkyl," as used in this specification, whether alone or as part of another group (e.g., in dialkylamino), encompasses straight and branched chain aliphatic groups having the indicated number of carbon atoms. If no number is indicated, alkyl preferably has 1-15 carbon atoms, more preferably 1-10 carbon atoms, and even more preferably 5-7 carbon atoms. Preferred alkyl groups include, without limitation, methyl, ethyl, propyl, isopropyl, butyl, isobutyl, sec-butyl, tert-butyl, pentyl, hexyl, heptyl, octyl, nonyl, decyl, and undecyl.

The term "alkenyl" as used in this specification means an unsaturated straight or branched chain aliphatic group having the indicated number of carbon atoms and containing one or more carbon-carbon double bonds. If no carbon number is indicated, the group preferably contains 2-15 carbon atoms, more preferably 2-10 carbon atoms, and further preferably 5-7 carbon atoms. Preferred alkenyl groups include, without limitation, ethenyl, propenyl, butenyl, pentenyl, and hexenyl.

The term "cycloalkyl" as employed herein included saturated and partially unsaturated cyclic hydrocarbon groups having 3 to 15 carbons. "Cycloalkyl" includes fused multicyclic systems, e.g., bicyclic and tricyclic systems such as octahydroindenyl, decahydronaphthalenyl, adamantanyl, and norbornanyl. Preferred cycloalkyl groups include, without limitation, cyclopropyl, cyclobutyl, cyclopentyl, cyclopentenyl, cyclohexyl, cyclohexenyl, cycloheptyl, and cyclooctyl.

An "aryl" group as a $C_6$-$C_{11}$ aromatic moiety comprising one to three aromatic rings. Preferably, the aryl group is a $C_6$-$C_{10}$ aryl group. Preferred aryl groups include, without limitation, phenyl, naphthyl, anthracenyl, and fluorenyl. More preferred is phenyl. "Arylalkyl" or "aralkyl" refers to an aryl group attached to the parent molecular moiety through an alkyl group, as defined above.

The following examples are illustrative of the invention, but are not intended to limit its scope. Those having skill in the art will recognize that the starting materials and reaction conditions may be varied, the sequence of the reactions altered, and additional steps employed to produce compounds encompassed by the present disclosure, as demonstrated by the following examples. Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Starting materials can be obtained from commercial sources or prepared by well-established literature methods known to those of ordinary skill in the art. The reactions may be performed in a solvent appropriate to the reagents and materials employed and suitable for the transformations being effected. Alternatively, one of the starting materials may serve as a solvent either at ambient or elevated temperature.

EXAMPLES

Alkyl ethers of sugar alcohols are prepared using a modified version of reductive etherification disclosed in the earlier application: M. L. Tulchinsky, J. R. Briggs, C. L. Rand, "Polyol Ethers and Process for Making Them," WO 2010027663 published 2010-03-11. Comparative Example 1 below demonstrates that the attempted use of the previous reductive etherification protocol from WO 2010027663 leads to unsatisfactory results. In the modified reductive etherification process of the examples below, the sugar alcohol is melted prior to the reaction.

The scheme below illustrates the scope of synthetic examples for the reductive etherification of $C_6$-$C_8$ aldehydes with $C_4$-$C_6$ sugar alcohols.

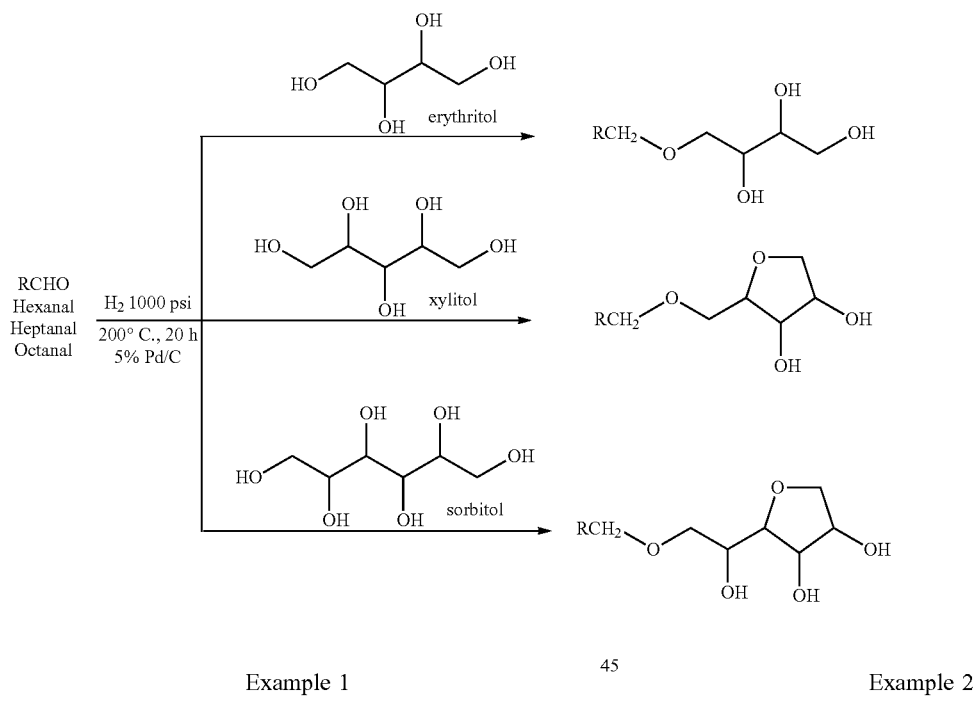

Example 1

Synthesis of 2-(2-heptyloxy-1-hydroxyethyl)-tetrahydrofuran-3,4-diol

Solid D-sorbitol 0.04554 kg (45.54 g) (0.25 mol) and 0.00031 kg (0.31 g) of 5% Pd/C catalyst are charged into a 0.00015 m³ (150 mL) Parr reactor containing an imbedded metal filter. The reactor is purged with hydrogen three times and then heated to about 110 degrees Celsius with careful stirring to melt D-sorbitol. Then, distilled heptanal (0.00457 kg (4.57 g) (0.04 mol)) is quickly added by syringe. After introducing hydrogen at an initial pressure of about 3.45× 10⁶ Pa (500 psi), the mixture is quickly heated to 200 degrees Celsius and the hydrogen pressure is set at about 6.89×10⁶ Pa (1000 psi). After 20 hours, the reactor is cooled, then methanol is added (0.00005 m³ (50 mL)×2) at a temperature of about 50 degrees Celsius and the solution is filtered through the reactor filter. Then methanol is evaporated, the residue is dissolved in water (0.00008 m³ (80 mL)) and extracted with diethyl ether (0.00005 m³ (50 mL)×8). The combined ether extracts are dried with sodium sulfate and the solvent is evaporated to give the crude product (0.00951 kg (9.51 g)), which is purified by flash chromatography on silica gel using hexane-ethyl acetate 2:1. The structure is elucidated by MS (M⁺+1=263) and NMR spectra. ¹H (ppm, δ, CDCl₃): 0.90 t (3H, CH₃—), 1.31 m (8H, —(CH₂)₄), 1.61 m (2H, β-CH₂—), 3.5-4.3 m (13H, sorbitan moiety). ¹³C NMR (ppm, δ, CDCl₃): 14.41, 22.94, 26.32, 29.46, 29.84, 32.13 (six carbons of the heptyl chain); 69.68, 72.18, 72.43, 73.86, 77.71, 78.01, 80.24 (sorbitan moiety).

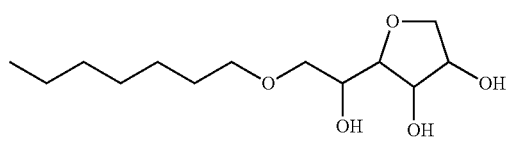 [SMILES: CCCCCCCOCC(O)C1OCC(O)C1O]

Example 2

Synthesis of 2-(2-hexyloxy-1-hydroxyethyl)-tetrahydrofuran-3,4-diol

The procedure in Example 1 is repeated using an equivalent molar amount of hexanal in place of heptanal and 5 weight percent of the same catalyst relative to the aldehyde. The structure is elucidated by MS (M⁺+1=249) and NMR spectra. ¹H (ppm, δ, CDCl₃): 0.91 t (3H, CH₃—), 1.32 m (6H, —(CH₂)₃—), 1.61 m (2H, β-CH₂—), 3.4-4.3 m (13H, sorbitan moiety). ¹³C NMR (ppm, δ, CDCl₃): 14.37, 22.93, 26.02, 29.79, 31.98 (five carbons of the hexyl chain); 69.72, 72.17, 72.41, 73.87, 77.71, 78.10, 80.25 (sorbitan moiety).

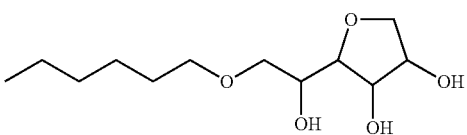 [SMILES: CCCCCCOCC(O)C1OCC(O)C1O]

Example 3

Synthesis of 2-(2-octyloxy-1-hydroxyethyl)-tetrahydrofuran-3,4-diol

The procedure in Example 1 is repeated using an equivalent molar amount of octanal in place of heptanal and 5 weight percent of the same catalyst relative to the aldehyde. The product is identified by MS (M$^+$+1=277) and NMR spectra. $^1$H (ppm, δ, CDCl$_3$): 0.90 t (3H, CH$_3$—), 1.29 m (10H, —(CH$_2$)$_5$—), 1.62 m (2H, β-CH$_2$—), 1.99 s broad (1H, OH), 2.58 s broad (1H, OH), 3.26 s broad (1H, OH), 3.5-4.4 m (10H, sorbitan protons minus 3 OH). $^{13}$C NMR (ppm, δ, CDCl$_3$): 14.43, 22.99, 26.40, 29.57, 29.74, 29.87, 32.14 (seven carbons of the octyl chain); 70.06, 72.17, 72.19, 73.90, 77.82, 78.48, 80.29 (sorbitan moiety).

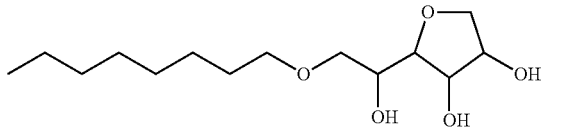 [SMILES: CCCCCCCCOCC(O)C1OCC(O)C1O]

Example 4

Synthesis of 2-(heptyloxymetyl)-tetrahydrofuran-3,4-diol

The procedure in Example 1 is repeated using an equivalent molar amount of xylitol in place of D-sorbitol. The product is identified by MS (M$^+$+1=233) and NMR spectra. $^1$H (ppm, δ, CDCl$_3$): 0.90 t (3H, CH$_3$—), 1.31 m (8H, —(CH$_2$)$_4$—), 1.61 m (2H, β-CH$_2$—), 3.5-4.3 m (13H, sorbitan moiety). $^{13}$C NMR (ppm, δ, CDCl$_3$): 14.37, 22.91, 26.26, 29.38, 29.81, 32.05 (alkyl chain); 70.03, 72.63, 73.68, 78.06, 78.63, 79.09 (anhydro-xylitol moiety).

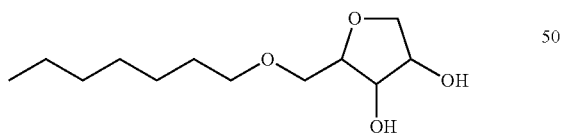

Example 5

Synthesis of 2-(hexyloxymetyl)-tetrahydrofuran-3,4-diol

The procedure in Example 1 is repeated using an equivalent molar amount of xylitol in place of D-sorbitol, an equivalent molar amount of hexanal in place of heptanal, and 5 weight percent of the same catalyst relative to the aldehyde. The product is identified by MS (M$^+$+1=219) and NMR spectra. $^1$H (ppm, δ, CDCl$_3$): 0.90 t (3H, CH$_3$—), 1.31 m (6H, —(CH$_2$)$_3$—), 1.59 m (2H, β-CH$_2$—), 2.23 s broad (1H, OH), 2.92 s broad (OH), 3.5-4.3 m (9H, hydrophile). $^{13}$C NMR (ppm, δ, CDCl$_3$): 14.33, 22.87, 25.99, 29.78, 31.90 (five carbons of the hexyl chain); 70.13, 72.70, 73.77, 78.20, 78.50, 59.36 (anhydro-xylitol moiety).

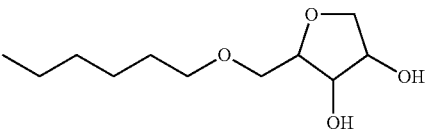

Example 6

Synthesis of 2-(heptyloxy)butane-1,2,3-triol

The procedure in Example 1 is repeated using an equivalent molar amount of meso-erythritol in place of D-sorbitol. The product is identified by MS (M$^+$+1=221) and NMR spectra. $^1$H (ppm, δ, CDCl$_3$): 0.91 t (3H, CH$_3$—), 1.32 m (8H, —(CH$_2$)$_4$—), 1.61 m (2H, β-CH$_2$—), 2.84 t broad (OH), 3.08 d broad (OH), 3.20 d broad (OH), 3.51 t (2H, CH$_2$O), 3.62 m and 3.80 m (6H, erythritol moiety). $^{13}$C NMR (ppm, δ, CDCl$_3$): 14.41, 22.94, 26.37, 29.44, 29.90, 32.11 (alkyl chain); 63.90, 71.29, 72.15, 72.19, 73.11 (CH$_2$O, erythritol moiety).

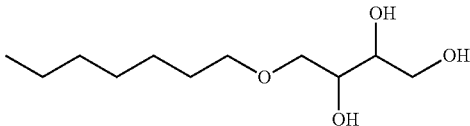

Example 7

Synthesis of 2-(hexyloxymetyl)butane-1,2,3-triol

The procedure in Example 1 is repeated using an equivalent molar amount of meso-erythritol in place of D-sorbitol, an equivalent molar amount of hexanal in place of heptanal, and 5 weight percent of the same catalyst relative to the aldehyde. The product is identified by MS (M$^+$+1=207) and NMR spectra. $^1$H (ppm, δ, CDCl$_3$): 0.91 t (3H, CH$_3$—), 1.32 m (6H, —(CH$_2$)$_3$—), 1.60 m (2H, β-CH$_2$—), 2.47 s broad (1H, OH), 3.1 s broad (1H, OH), 3.38 s broad (1H, OH), 3.50 t (2H, CH$_2$O), 3.61 m and 3.76 m (6H, erythritol moiety). $^{13}$C NMR (ppm, δ, CDCl$_3$): 14.35, 22.91, 26.05, 29.83, 31.96 (five carbons of the hexyl chain); 63.80, 71.27, 72.17, 72.20, 73.09 (erythritol moiety).

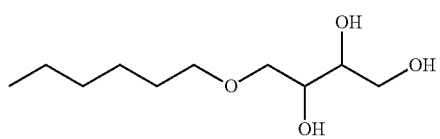

Example 8

Synthesis of 2-(2-ethylhexyloxy-1-hydroxyethyl)-tetrahydrofuran-3,4-diol

The procedure in Example 2 is repeated using an equivalent molar amount of 2-ethylhexanal in place of heptanal and 5 weight percent of the same catalyst relative to the aldehyde. The structure was elucidated by MS ($M^++1=277$) and NMR spectra. $^1$H (ppm, δ, CDCl$_3$): 0.91 t (6H, two CH$_3$ groups), 1.32 m (8H, four CH$_2$ groups), 1.61 m (1H, CH), 2.9-4.3 m (13H, sorbitan moiety). $^{13}$C NMR (ppm, δ, CDCl$_3$): 11.38, 14.42, 23.38, 24.18, 29.40, 30.82, 39.86 (seven carbons of the 2-ethylhexyl chain); 70.04, 72.50, 73.89, 74.87, 77.78, 78.48, 80.36 (sorbitan moiety).

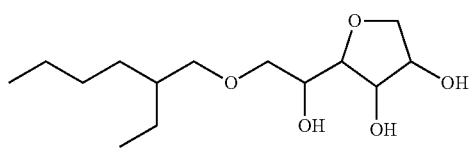 [SMILES: CCCCC(CC)COCC(O)C1OCC(O)C1O]

area percent of dioctyl ether ($M^++1=243$ in GC/MS) and contains only about 6 GC area percent of the desired product.

Example 9

Surface Tension and Critical Micelle Concentration of 2-(2-heptyloxy-1-hydroxyethyl)-tetrahydrofuran-3,4-diol The critical micelle concentration (CMC) and the surface tension of 2-(2-heptyloxy-1-hydroxyethyl)-tetrahydrofuran-3,4-diol are evaluated. The sample is diluted to a 1% aqueous solution in a 0.000001 m$^3$ (1 mL) vial. A total of 12 dilutions starting at 1 weight percent are prepared. The concentration of each dilution is recorded in the table below. Surface tension of all twelve diluted samples is measured using a Kibron Delta-8 multichannel microtensiometer. The Kibron microtensiometer measures surface tension by maximum pull force/du Nouy method. The eight channel wire probes are cleaned internally in the instrument by heating. The sample volume for each analysis is 5.0×10$^8$ m$^3$ (50 uL). The results are shown in Table 2 below. The instrument is calibrated using Nanopure water. The surface tension of Example 9 at 1 weight percent concentration is 0.0274 N/m (27.4 dynes/cm). The CMC is about 2500 ppm. The effect of concentration of the sample on surface tension is shown in FIG. 1.

TABLE 2

Kibron Delta-8 Microtensiometer Data for Example 9 (2-(2-heptyloxy-1-hydroxyethyl)-tetrahydrofuran-3,4-diol)

| | Sample | | | | | | |
|---|---|---|---|---|---|---|---|
| | 1 | 2 | 3 | 4 | 5 | 6 | 7 |
| Weight percent | 1 | 0.5 | 0.25 | 0.125 | 0.0625 | 0.03125 | 0.015625 |
| ppm | 10000.00 | 5000.00 | 2500.00 | 1250.00 | 625.00 | 312.50 | 156.25 |
| Surface tension N/m (dynes/cm) | 0.0274 (27.4) | 0.0282 (28.2) | 0.0284 (28.4) | 0.0347 (34.7) | 0.0433 (43.3) | 0.0551 (55.1) | 0.0663 (66.3) |

| | Sample | | | | |
|---|---|---|---|---|---|
| | 8 | 9 | 10 | 11 | 12 |
| Weight percent | 0.007813 | 0.003906 | 0.001953 | 0.000977 | 0.000488 |
| ppm | 78.13 | 39.06 | 19.53 | 9.77 | 4.88 |
| Surface tension N/m (dynes/cm) | 0.0711 (71.1) | 0.0724 (72.4) | 0.0726 (72.6) | 0.0729 (72.9) | 0.0728 (72.8) |

Comparative Example 1

Attempted synthesis of 2-(2-octyloxy-1-hydroxyethyl)-tetrahydrofuran-3,4-diol The procedure in Example 3 is repeated, but both D-sorbitol and octanal are charged in the reactor together along with the catalyst. The crude product contains about 67 GC

Example 10

Figure 2:
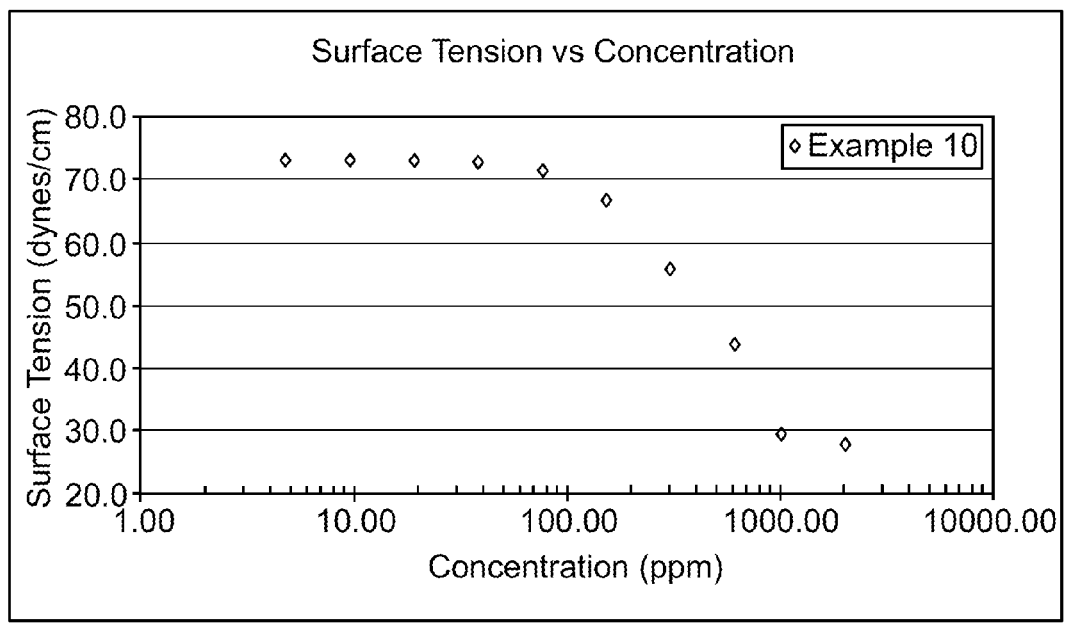
FIG. 2 is a graph of surface tension versus concentration for Example 10.

Surface Tension and Critical Micelle Concentration of 2-(2-octyloxy-1-hydroxyethyl)-tetrahydrofuran-3,4-diol The critical micelle concentration (CMC) and the surface tension of 2-(2-octyloxy-1-hydroxyethyl)-tetrahydrofuran-3,4-diol are evaluated according to the procedure described in Example 9, except that the sample is diluted to a 0.2% aqueous solution in a 0.000001 m³ (1 mL) vial. A total of 10 dilutions starting at 0.2 weight percent are prepared for the sample. The concentration of each dilution is shown in Table 3 below. The surface tension of Example 10 at 0.2 weight percent concentration is 0.0275 N/m (27.6 dynes/cm). The CMC is about 1000 ppm. The effect of concentration of the sample on surface tension is shown in FIG. 2.

TABLE 3

Kibron Delta-8 Microtensiometer Data for Example 9 (2-(2-octyloxy-1-hydroxyethyl)-tetrahydrofuran-3,4-diol)

| | Sample | | | | | | |
|---|---|---|---|---|---|---|---|
| | 1 | 2 | 3 | 4 | 5 | 6 | 7 |
| Weight percent | 0 | 0 | 0.2 | 0.1 | 0.05 | 0.025 | 0.0125 |
| Ppm | 0.00 | 0.00 | 2000.00 | 1000.00 | 500.00 | 250.00 | 125.00 |
| Surface tension N/m (dynes/cm) | 0.0 (0.0) | 0.0 (0.0) | 0.0276 (27.6) | 0.0295 (29.5) | 0.0424 (42.4) | 0.0547 (54.7) | 0.0618 (61.8) |

| | Sample | | | | |
|---|---|---|---|---|---|
| | 8 | 9 | 10 | 11 | 12 |
| Weight percent | 0.0625 | 0.003125 | 0.001563 | 0.000781 | 0.000391 |
| Ppm | 62.50 | 31.25 | 15.63 | 7.81 | 3.91 |
| Surface tension N/m (dynes/cm) | 0.0692 (69.2) | 0.0711 (71.1) | 0.0722 (72.2) | 0.0726 (72.6) | 0.0728 (72.8) |

Comparative Example 2

Surface Tension and Critical Micelle Concentration of $C_7$ Ethers with $C_4$ and $C_5$ Sugar Alcohols ($C_4$ Erythritol and $C_5$ Xylitol) to Compare with Example 9 ($C_7$ Ether with $C_6$ Sorbitol)

Figure 3:
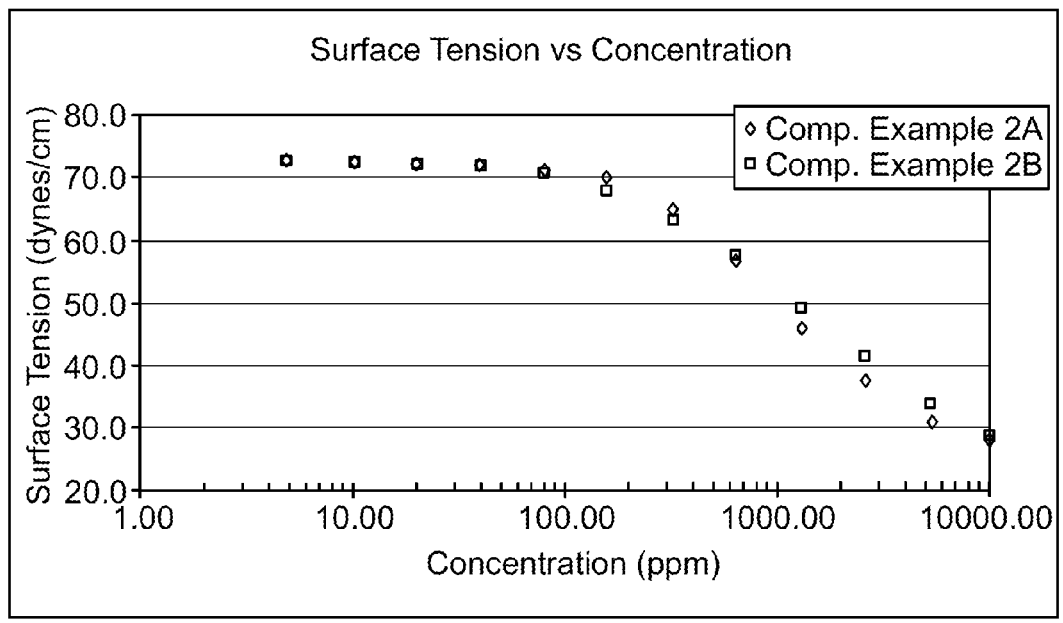
FIG. 3 is a graph of surface tension versus concentration for Comparative Examples 2A and 2B.

The critical micelle concentration (CMC) and the surface tension of $C_7$ ethers with $C_4$ and $C_5$ sugar alcohols are evaluated according to the procedure described in Example 9. $C_7$ ethers of erythritol ($C_4$ sugar) and xylitol ($C_5$ sugar) have high CMC values (>10000 ppm and >5000 ppm respectively), whereas the $C_7$ ether of sorbitol ($C_6$ sugar) has a CMC at about 2500 ppm, as shown in Table 4 below. Hence, $C_7$ ether of sorbitol (Example 9) can form micelles at a much lower concentration than those of erythritol and xylitol. The effect of concentration of the samples on surface tension is shown in FIG. 3.

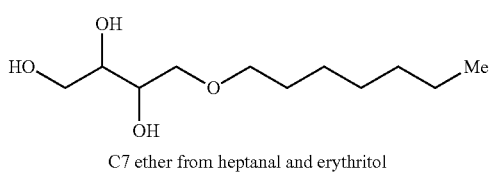

comparative example 2A

C7 ether from heptanal and erythritol

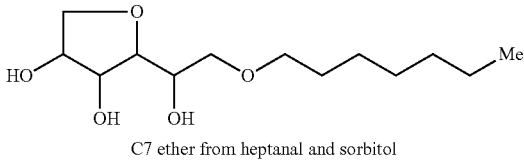

comparative example 2B

C7 ether from heptanal and xylitol

-continued

Example 9

C7 ether from heptanal and sorbitol

TABLE 4

Surface tension and CMC of $C_7$ ethers

| | Surface tension (1%) N/m (Dynes/cm) | CMC (ppm) |
|---|---|---|
| Comp. Example 2A | 0.0279 (27.9) | >10000 |
| Comp. Example 2B | 0.0287 (28.7) | >5000 |
| Example 9 | 0.0274 (27.4) | 2500 |

Comparative Example 3

Surface Tension and Critical Micelle Concentration of $C_6$ Ethers Alcohols $C_4$ Erythritol, $C_5$ Xylitol, and $C_6$ Sorbitol) to Compare with Example 9 ($C_7$ Ether with Sorbitol)

Figure 4:
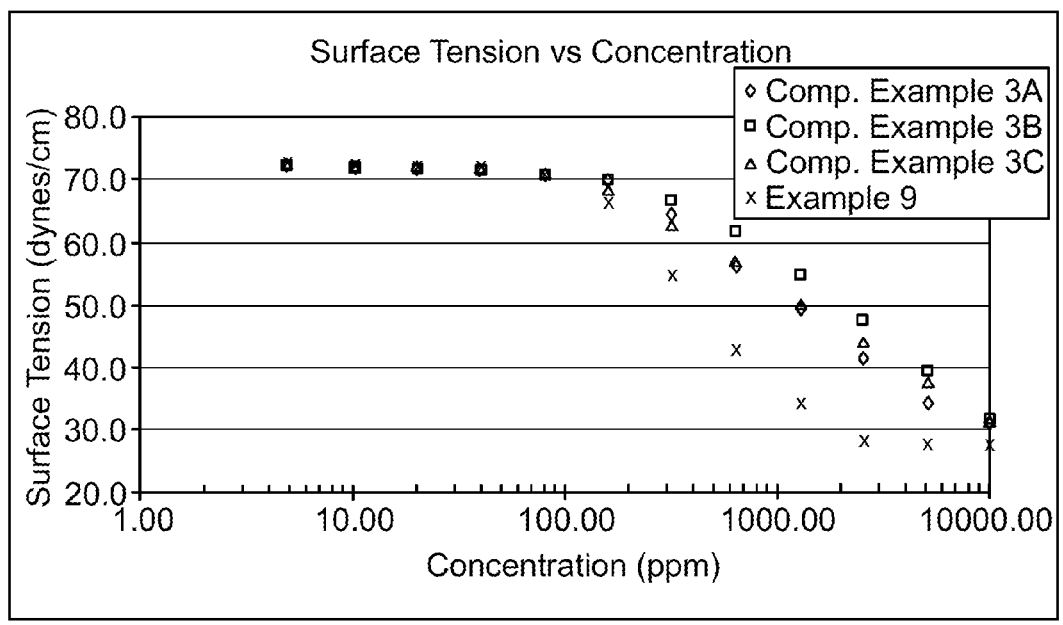
FIG. 4 is a graph of surface tension versus concentration for Comparative Examples 3A, 3B, and 3C and Example 9.

The critical micelle concentration (CMC) and the surface tension of $C_6$ ethers with $C_4$-$C_6$ sugar alcohols are evaluated according to the procedure described in Example 9. $C_6$ ethers of erythritol ($C_4$ sugar), xylitol ($C_5$ sugar), and sorbitol ($C_6$ sugar) have high CMC values (>10000 ppm), whereas the $C_7$ ether of sorbitol ($C_6$ sugar) has a CMC at about 2500 ppm, as shown in Table 5 below. Hence, $C_7$ ether of sorbitol (Example 9) can form micelles at a much lower concentration than those of $C_6$ ethers. The effect of concentration of the samples on surface tension is shown in FIG. 4.

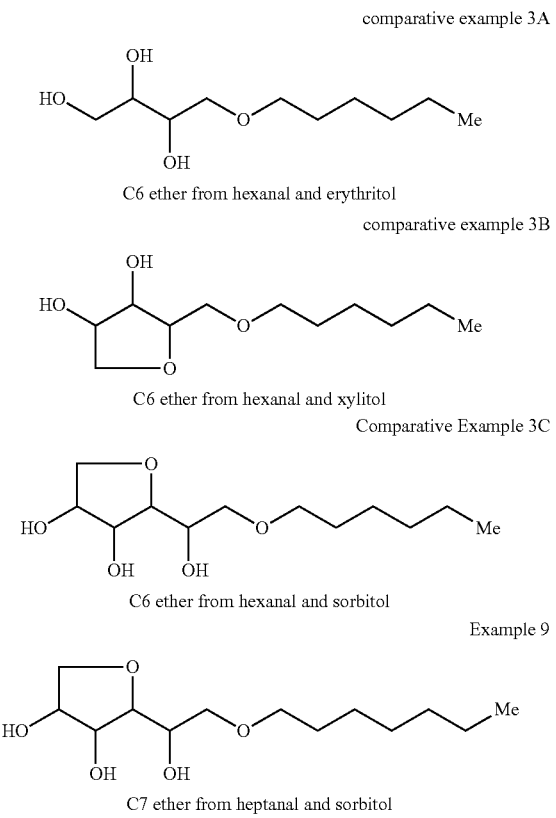

TABLE 5

Surface tension and CMC of $C_6$ ethers

|  | Surface tension (1%) N/m (Dynes/cm) | CMC (ppm) |
|---|---|---|
| Comp. Example 3A | 0.0310 (31.0) | >10000 |
| Comp. Example 3B | 0.0320 (32.0) | >10000 |
| Comp. Example 3C | 0.0318 (31.8) | >10000 |
| Example 9 | 0.0274 (27.4) | 2500 |

Example 11

Hard Surface Cleaning Performance on Vinyl Tile

Soil removal from a hard surface such as vinyl tiles can be facilitated by a surfactant. A modified scrubbing test based on the Gardner scrub test (ASTM D-2486) is used to evaluate the hard surface cleaning efficiency of sugar ether surfactants. The level of cleaning is determined by the grey value of the scrubbed spot after the scrubbing. The larger the grey value, the whiter the scrubbed area and thus the better the cleaning efficiency.

Soil of the formula shown in Table 6 below is spread over a vinyl tile using a foam brush. The tile is air-dried in a fume hood overnight. The sample is added to the vinyl tile and the tile is placed on a shaker. The vinyl tile is scrubbed with a scrubber when the shaker is turned on. An image of the tile is recorded and the grey scale is analyzed. Four replicates for each sample are performed.

TABLE 6

Hard Surface Cleaning Soil Recipe

| Naphtha 60/110 | 61.06% |
|---|---|
| Edenor EV 85 BR (C8-C10 fatty acid) | 27.62% |
| Soybean oil | 8.15% |
| Carbon black | 3.17% |

Figure 5:
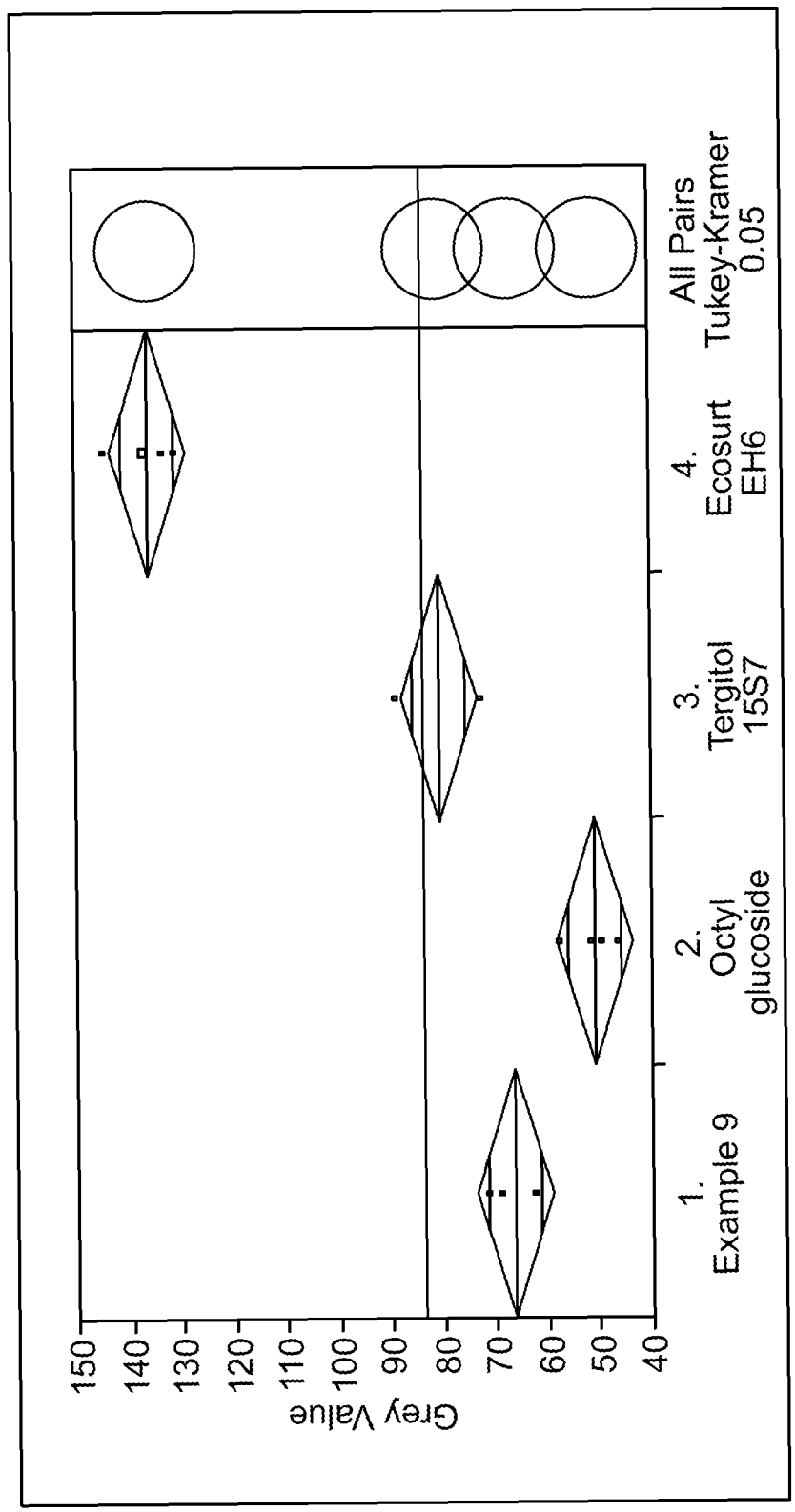
FIG. 5 is a graph of grey values for Example 9, octyl glucoside, TERGITOL™ 15-S-7 and ECOSURF™ EH-6.

It is demonstrated by the grey scale analysis, as shown in FIG. 5, that Example 9 has significantly improved cleaning efficiency (mean grey scale of 67) from a similar octyl glucoside (mean grey scale of 51). Example 9 has comparable cleaning efficiency as TERGITOL™ 15-S-7 surfactant (mean grey scale of 80).

Example 12

Alternative Process

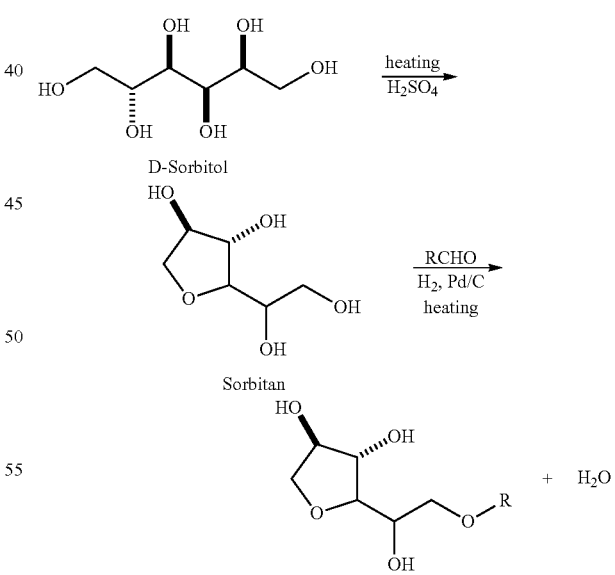

In an alternative example, D-sorbitol is heated at ambient pressure to form sorbitan.

Methods for the preparation of sorbitan from D-sorbitol can be found in the literature. See, e.g., U.S. Pat. No. 6,441,196; Alain Duclos et al., *A simple conversion of polyols into anhydroalditols*, Synthesis 1087-90 (2004); Sol Soltzberg et al., *Hexitol anhydrides. Synthesis and structure*

*of arlitan, the* 1, 4-*monoanhydride of sorbitol*, J. of the Am. Chemistry Society 919-21 (1946). The procedures in Examples 1-3 are repeated using sorbitan in place of D-sorbitol.

Sorbitan and 5% Pd/C catalyst are charged into a Parr reactor containing an imbedded metal filter. The reactor is purged with hydrogen three times and then heated to about 110 degrees Celsius. Then distilled heptanal is quickly added by syringe. After introducing hydrogen at an initial pressure of about $3.45 \times 10^6$ Pa (500 psi), the mixture is quickly heated to 200 degrees Celsius and the hydrogen pressure is set at about $6.89 \times 10^6$ Pa (1000 psi). After 20 hours, the reactor is cooled, then methanol is added (0.00005 m$^3$ (50 mL)×2) at a temperature of about 50 degrees Celsius and the solution is filtered through the reactor filter. Then methanol is evaporated, the residue is dissolved in water (0.00008 m$^3$ (80 mL)) and extracted with diethyl ether (0.00005 m$^3$ (50 mL)×8). The combined ether extracts are dried with sodium sulfate and the solvent is evaporated to give the crude product, which is purified by flash chromatography on silica gel using hexane-ethyl acetate 2:1.

Example 13

Preparation of a Derivative with Two Sorbitan Moieties

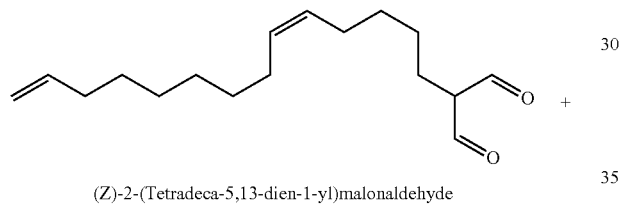

(Z)-2-(Tetradeca-5,13-dien-1-yl)malonaldehyde

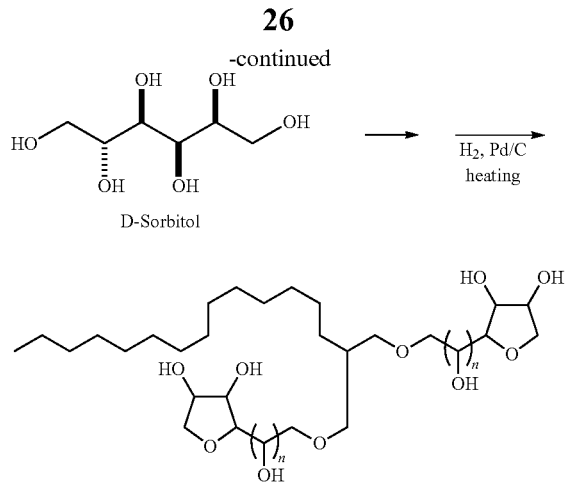

The procedure in Example 1 is repeated using a dialdehyde in place of heptanal. This dialdehyde is prepared as described in J. K. Staples at al. *J. Chem. Ecol.* 2009, 35 (12), 1448-1460. The sorbitol/dialdehyde molar ratio is greater than 10:1 (sorbitol/one aldehyde group is greater than 5:1).

Example 14

Preparation of a Derivative with One Sorbitan and One Ester Group

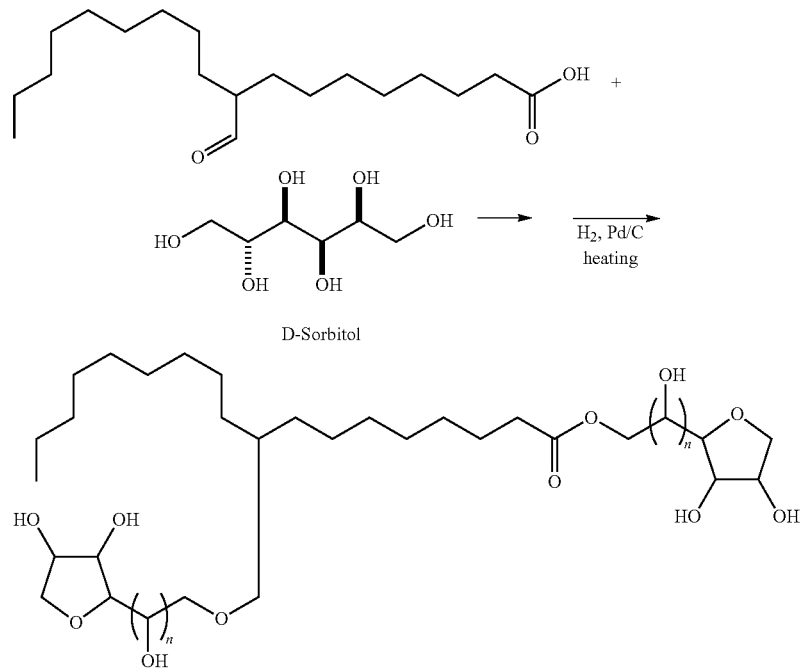

The procedure in Example 1 is repeated using an aldehyde ester in place of heptanal. The aldehyde ester may be prepared, for example, according to C. H. McKeever, G. H. Agnew, U.S. Pat. No. 2,533,276 to Rohm & Haas. The sorbitol/aldehyde ester molar ratio is greater than 10:1.

While the invention has been described above according to its preferred embodiments, it can be modified within the spirit and scope of this disclosure. This application is therefore intended to cover any variations, uses, or adaptations of the invention using the general principles disclosed herein. Further, the application is intended to cover such departures from the present disclosure as come within the known or customary practice in the art to which this invention pertains and which fall within the limits of the following claims.

What is claimed is:

1. A process comprising:
   melting a polyol; and
   reacting the molten polyol, a carbonyl compound and hydrogen in the presence of a hydrogenation catalyst to produce a polyol ether of formula I

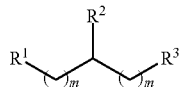

wherein $R^1$ is ($C_1$-$C_{10}$) alkyl;
$R^2$ is hydrogen; and
$R^3$ is

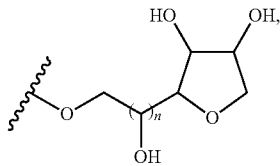

wherein m is zero wherein n is 0.

2. The process according to claim 1, wherein carbonyl compound is of formula II:

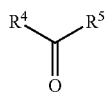

wherein $R^4$ and $R^5$ are ($C_5$-$C_7$) alkyl.

3. The process according to claim 1, wherein the polyol is a sugar alcohol.

4. A compound according to the following formula:

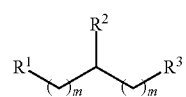

wherein $R^1$ is ($C_1$-$C_{10}$) alkyl,
$R^2$ is hydrogen; and
$R^3$ is

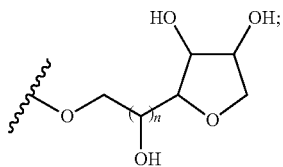

wherein each m is zero and wherein n is 0.

5. The compound according to claim 4, wherein $R^1$ is ($C_5$-$C_7$) alkyl.

* * * * *